(12) United States Patent
Starzewski et al.

(10) Patent No.: US 6,232,413 B1
(45) Date of Patent: May 15, 2001

(54) METHOD FOR PRODUCING CYCLOOLEFIN (CO) POLYMERS FOR USE IN OPTICAL DATA MEMORIES

(75) Inventors: Karl-Heinz Aleksander Ostojola Starzewski, Bad Vilbel (DE); Warren Mark Kelly, Airdrie (CA); Andreas Stumpf; Claudia Schmid, both of Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/214,206

(22) PCT Filed: Jul. 2, 1997

(86) PCT No.: PCT/EP97/03459

§ 371 Date: Dec. 30, 1998

§ 102(e) Date: Dec. 30, 1998

(87) PCT Pub. No.: WO98/01483

PCT Pub. Date: Jan. 15, 1998

(30) Foreign Application Priority Data

Jul. 5, 1996 (DE) ................................. 196 27 064
Apr. 5, 1997 (DE) ................................. 197 14 058

(51) Int. Cl.$^7$ ............................. C08F 4/44; C08F 232/04
(52) U.S. Cl. ........................... 526/134; 526/281; 526/161; 526/943; 502/152
(58) Field of Search ..................................... 526/160, 161, 526/943, 171, 172, 348, 281, 308, 348.6, 319, 335, 282, 131, 346, 134

(56) References Cited

U.S. PATENT DOCUMENTS

| | | | |
|---|---|---|---|
| 5,324,800 | 6/1994 | Welborn, Jr. et al. | 526/160 |
| 5,545,829 | 8/1996 | Brekner et al. | 526/160 |
| 5,567,777 | 10/1996 | Tsuji et al. | 525/289 |
| 5,580,939 | 12/1996 | Ewen et al. | 526/127 |
| 5,602,219 | 2/1997 | Aulbach et al. | 526/160 |
| 5,633,394 | 5/1997 | Welborn, Jr. et al. | 556/11 |
| 5,723,635 | 3/1998 | Durand et al. | 549/610 |
| 5,756,417 * | 5/1998 | De Boer et al. | 502/117 |

FOREIGN PATENT DOCUMENTS

| | | |
|---|---|---|
| 2151558 | 12/1995 | (CA) . |
| 0 638 593 A1 * | 2/1995 | (EP) . |
| 636 593 | 2/1995 | (EP) . |
| 704 461 | 4/1996 | (EP) . |
| 94/20506 | 9/1994 | (WO) . |

* cited by examiner

Primary Examiner—David W. Wu
Assistant Examiner—R. Harlan
(74) Attorney, Agent, or Firm—Joseph C. Gil; Noland J. Cheung

(57) ABSTRACT

Cycloolefin copolymers for use for optical data memories, can be prepared by copolymerization of monomers from the group consisting of cyclic olefins, α-olefins having 2 or more C atoms and optionally conjugated or non-conjugated diolefins, the catalysts employed being metallocene compounds or π complex compounds of the formula

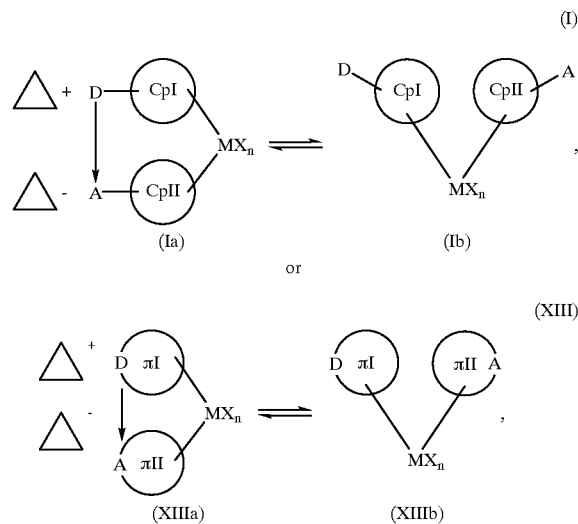

in which CpI and CpII represent carbanions having a cyclopentadienyl-containing structure, πI and πII represent charged or electrically neutral π systems, D represents a donor atom and A represents an acceptor atom, where D and A are linked by a reversible coordinate bond such that the donor group assumes a positive (part) charge and the acceptor group assumes a negative (part) charge, M represents a transition metal of sub-group III, IV, V or VI of the Periodic Table of elements (Mendeleev), including the lanthanides and the actinides, X denotes an anion equivalent and n denotes the number zero, one, two, three or four, depending on the charge of M.

15 Claims, No Drawings

METHOD FOR PRODUCING CYCLOOLEFIN (CO) POLYMERS FOR USE IN OPTICAL DATA MEMORIES

FIELD OF THE INVENTION

The present invention relates to the use of π systems or of metallocene compounds in which a transition metal with two π systems, and in particular with aromatic π systems, such as anionic cyclopentadienyl ligands (carbanions) is complexed and the two systems are bonded reversibly to one another by at least one bridge of a donor and an acceptor, as organometallic catalysts in a process for the preparation of cycloolefin (co)polymers for use for optical data memories, by (co)polymerization of monomers from the group consisting of cyclic olefins, α-olefins having 2 or more C atoms and optionally conjugated for non-conjugated diolefins. The coordinate bond formed between the donor atom and the acceptor atom produces a positive (part) charge in the donor group and a negative (part) charge in the acceptor group:

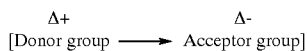

BACKGROUND OF THE INVENTION

Cycloolefin (co)polymers are distinguished by many advantageous properties, for example by a high transparency for use for their application in the field of optical data memories, in particular for compact disks (CDs) of high memory density. They furthermore have a good heat resistance, resistance to aging, resistance to chemicals, resistance to solvents, low absorption of water, high scratch resistance, low birefringence of light and high softening points (glass transition temperatures $T_g$).

Metallocenes and their use as catalysts in the polymerization of olefins have been known for a long time (EP-A 129 368 and the literature cited therein). It is furthermore known from EP-A '368 that metallocenes in combination with aluminum-alkyl/water as cocatalysts are active systems for the polymerization of ethylene (thus, for example, methylaluminoxane=MAO is formed from 1 mol of trimethylaluminum and 1 mol of water. Other stoichiometric ratios have also already been used successfully (WO 94/20506)). Metallocenes in which the cyclopentadienyl skeletons are linked to one another covalently via a bridge are also already known. An example of the numerous Patents and Applications in this field which may be mentioned is EP-A 704 461, in which the linkage group mentioned therein is a (substituted) methylene group or ethylene group, a silylene group, a substituted silylene group, a substituted germylene group or a substituted phosphine group. The bridged metallocenes are also envisaged as polymerization catalysts for olefins in EP '461. In spite of the numerous Patents and Applications in this field, there continues to be a demand for improved catalysts which are distinguished by a high activity, so that the amount of catalyst remaining in the polymer can be set to a low level, and which are equally suitable for the (co)polymerization of cycloolefins, for the preparation of which metallocenes have likewise already been employed (U.S. Pat. No. 5,567,777; EP 610 852=U.S. Pat. No. 5,602,219; EP 690 078).

SUMMARY OF THE INVENTION

It has now been found that particularly advantageous catalysts can be prepared from bridged π complex compounds, and in particular from metallocene compounds, in which the bridging of the two π systems is established by one, two or three reversible donor-acceptor bonds, in which in each case a coordinate or so-called dative bond which is overlapped at least formally by an ionic bond forms between the donor atom and the acceptor atom, and in which one of the donor or acceptor atoms can be part of the particular associated π system. The reversibility of the donor-acceptor bond also allows, in addition to the bridged state identified by the arrow between D and A, the non-bridged state. π systems according to the invention which are to be employed, for example metallocenes, can therefore be described by a double arrow and the formula part (Ia) and (Ib) or (XIIIa) and (XIIIb) to include both steps.

DETAILED DESCRIPTION OF THE INVENTION

The invention accordingly relates to a process for the preparation of cycloolefin (co)polymers for use for optical data memories, by (co)polymerization of monomers from the group consisting of cyclic olefins, α-olefins having 2 or more C atoms and optionally conjugated or non-conjugated diolefins in the gas, bulk, solution or slurry phase at −78 to +200° C. under 0.5–70 bar in the presence of organometallic catalysts which can be activated by cocatalysts, which comprises employing as the organometallic catalysts metallocene compounds of the formula

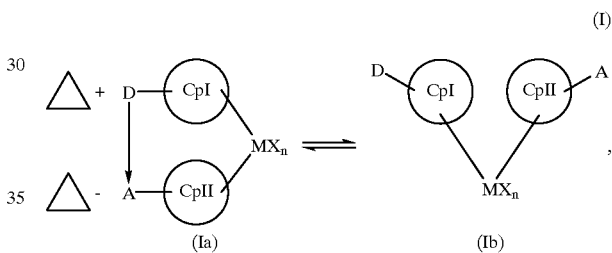

(I)

in which
  CpI and CpII are two identical or different carbanions having a cyclopentadienyl-containing structure, in which one to all of the H atoms can be replaced by identical or different radicals from the group consisting of linear or branched $C_1$–$C_{20}$-alkyl, which can be monosubstituted to completely substituted by halogen, mono- to trisubstituted by phenyl or mono- to trisubstituted by vinyl, $C_6$–$C_{12}$-aryl, halogenoaryl having 6 to 12 C atoms, organometallic substituents, such as silyl, trimethylsilyl or ferrocenyl, and 1 or 2 can be replaced by D and A,
  D denotes a donor atom, which can additionally carry substituents and has at least one free electron pair in its particular bond state,
  A denotes an acceptor atom, which can additionally carry substituents and has an electron pair gap in its particular bond state,
  where D and A are linked by a reversible coordinate bond such that the donor group assumes a positive (part) charge and the acceptor group assumes a negative (part) charge,
  M represents a transition metal of sub-group III, IV, V or VI of the Periodic Table of the elements (Mendeleev), including the lanthanides and actinides,
  X denotes an anion equivalent and
  n denotes the number zero, one, two, three or four, depending on the charge of M, or π complex compounds, and in particular metallocene compounds of the formula

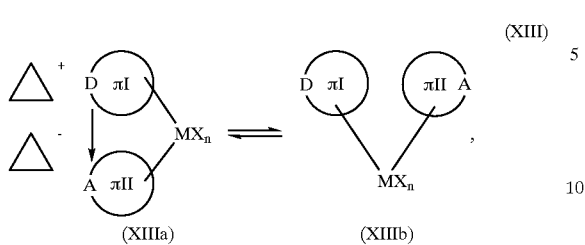

in which

π I and π II represent different charged or electrically neutral π systems which can be fused to one or two unsaturated or saturated five- or six-membered rings, D denotes a donor atom, which is a substituent of π I or part of the π system of π I and has at least one free electron pair in its particular bond state, A denotes an acceptor atom, which is a substituent of π II or part of the π system of π II and has an electron pair gap in its particular bond state, where D and A are linked by a reversible coordinate bond such that the donor group assumes a positive (part) charge and the acceptor group assumes a negative (part) charge, and where at least one of D and A is part of the particular associated π system, where D and A in turn can carry substituents, where each π system and each fused-on ring system can contain one or more D or A or D and A and where in π I and π II in the non-fused or in the fused form, one to all of the H atoms of the π system independently of one another can be replaced by identical or different radicals from the group consisting of linear or branched $C_1$–$C_{20}$-alkyl, which can be monosubstituted to completely substituted by halogen, mono- to trisubstituted by phenyl or mono- to trisubstituted by vinyl, $C_6$–$C_{12}$-aryl, halogenoaryl having 6 to 12 C atoms, organometallic substituents, such as silyl, trimethylsilyl or ferrocenyl, or one or two can be replaced by D and A, so that the reversible coordinate D→A bond is formed (i) between D and A, which are both parts of the particular π system or the fused-on ring system, or (ii) of which D or A is (are) part of the π system or of the fused-on ring system and in each case the other is (are) a substituent of the non-fused π system or the fused-on ring system, M and X have the above meaning and n denotes the number zero, one, two, three or four depending on the charges of M and those of π-I and π-II.

π systems according to the invention are substituted and unsubstituted ethylene, allyl, pentadienyl, benzyl, butadiene, benzene, the cyclopentadienyl anion and the species which result by replacement of at least one C atom by a heteroatom. Among the species mentioned, the cyclic species are preferred. The nature of the coordination of such ligands (π systems) to the metal can be of the σ type or of the π type.

Such metallocene compounds of the formula (I) which are to be employed according to the invention can be prepared by reacting with one another either in each case a compound of the formulae (II) and (III)

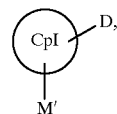

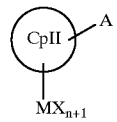

or in each case a compound of the formulae (IV) and (V)

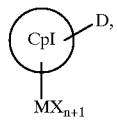

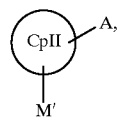

or in each case a compound of the formulae (VI) and (VII)

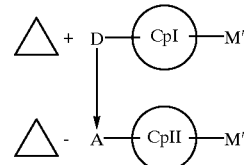

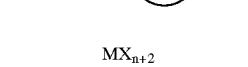

with elimination of M'X, in the presence of an aprotic solvent, or in each case a compound of the formulae (VIII) and (III)

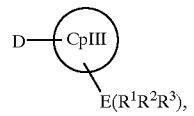

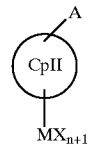

or in each case a compound of the formulae (IV) and (IX)

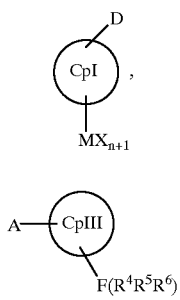
(IV)

(IX)

or in each case a compound of the formulae (X) and (VII)

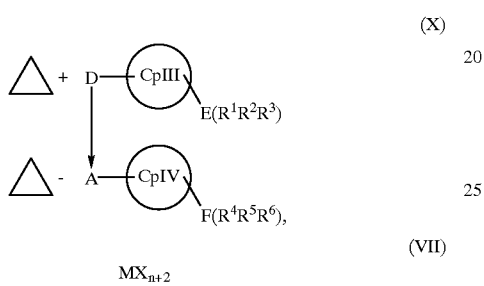
(X)

(VII)
$MX_{n+2}$ with elimination of $E(R^1R^2R^3)X$ and $F(R^4R^5R^6)X$, in the absence or in the presence of an aprotic solvent, in which CpI, CpII, D, A, M, X and n have the above meaning, CpIII and CpIV represent two identical or different non-charged molecular parts having a cyclopentadiene-containing structure, but are otherwise the same as CpI and CpII, M' denotes one cation equivalent of an alkali metal or alkaline earth metal or Tl, E and F independently of one another denote one of the elements Si, Ge or Sn and $R^1$, $R^2$, $R^3$, $R^4$, $R^5$ and $R^6$ independently of one another represent straight-chain or branched $C_1$–$C_{20}$-alkyl, $C_6$–$C_{12}$-aryl and $C_1$–$C_6$-alkyl-$C_6$–$C_{12}$-aryl and $C_6$–$C_{12}$-aryl-$C_1$–$C_6$-alkyl, vinyl, alkyl or halogen, and where furthermore, in the formulae (VIII), (IX) and (X), hydrogren can replace $E(R^1R^2R^3)$ and $F(R^4R^5R^6)$, and in this case X can also represent an amide anion of the type $R_2N^\ominus$ or a carbanion of the type $R_3C^\ominus$ or an alcoholic anion of the type $RO^\ominus$, and where furthermore it is possible to react compounds of the formulae (II) or (VIII) directly with a transition metal compound of the formula (VII) in the presence of compounds of the formulae (V) or (IX). Two anions X can furthermore be bonded to a dianion, if appropriate with interpolation of a single- or multi-atom bridge.

In the reaction of (VIII) with (III) or (IV) with (IX) or (X) with (VII), in the case of the variant mentioned last, the structure (I) forms with elimination of amine $R_2NH$ or $R_2NE(R^1R^2R^3)$ or $R_2NF(R^4R^5R^6)$ or a hydrocarbon compound of the formula $R_3CH$ or $R_3CE(R^1R^2R^3)$ or $R_3CF(R^4R^5R^6)$ or an ether $ROE(R^1R^2R^3)$ or $ROF(R^4R^5R^6)$, in which the organic radicals R are identical or different and independently of one another are $C_1$–$C_{20}$-alkyl, $C_6$–$C_{12}$-aryl, substituted or unsubstituted allyl, benzyl or hydrogen. Examples of the amine or hydrocarbon, ether, silane, stannane or germane eliminated are, for example, dimethylamine, diethylamine, di-(n-propyl)amine, di-(isopropyl)amine, di-(tert-butyl)amine, tert-butylamine, cyclohexylamine, aniline, methylphenylamine, di-(allyl) amine or methane, toluene, trimethylsilylamine, trimethylsilyl ether, tetramethylsilane and the like.

It is also possible to react compounds of the formulae (II) or (VIII) directly with a transition metal compound of the formula (VII) in the presence of compounds of the formulae (V) or (IX).

π complex compounds of the formula (XIII) in which the π systems are cyclic and aromatic (metallocenes) can be prepared analogously, the following compounds being employed accordingly:

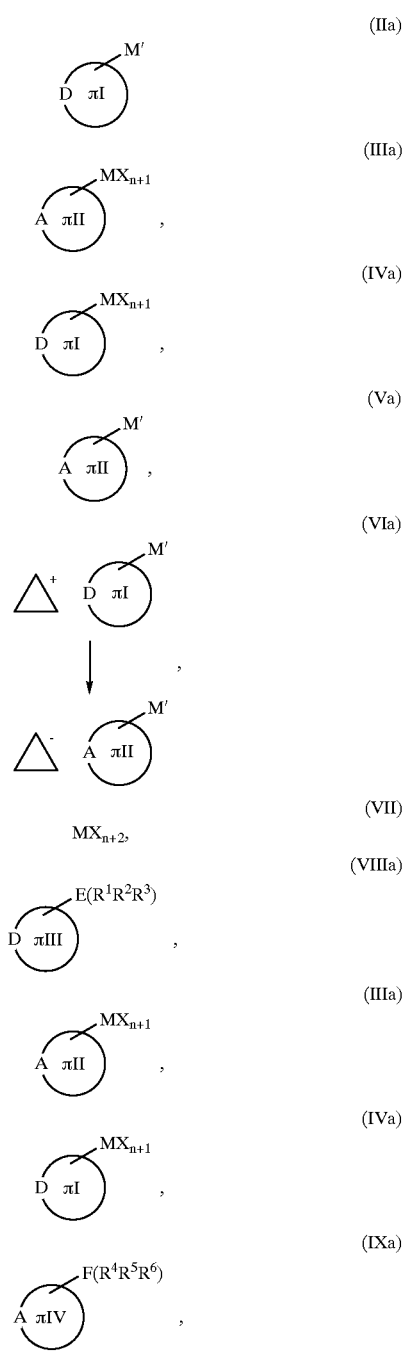

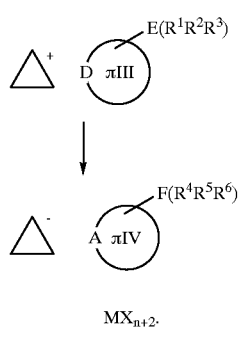

(Xa)

(VII)

Open-chain π complex compounds are prepared by processes known to the expert with incorporation of donor and acceptor groups.

According to the invention, the reaction is carried out in the gas, bulk, solution or slurry phase at −78 to −+200° C., preferably −50 to +150° C., particularly preferably −30 to +100° C., under 0.5 to 70 bar, preferably 1 to 50 bar, particularly preferably 1 to 20 bar, in the presence of absence of saturated or aromatic hydrocarbons or of saturated or aromatic halogeno hydrocarbons and in the presence or absence of hydrogen, the metallocene compounds or the π complex compounds being employed as catalysts in an amount of $10^1$ to $10^{12}$ mol of all the monomers per mole of metallocene or π complex compounds, and it being furthermore possible to carry out the reaction in the presence of Lewis acids, Brönstedt acids or Pearson acids, or additionally in the presence of Lewis bases.

Such Lewis acids are, for example, boranes or alanes, such as aluminum-alkyls, aluminum halides, aluminum alcoholates, organoboron compounds, boron halides, boric acid esters or compounds of boron or aluminum which contain both halide and alkyl or aryl or alcoholate substituents, and mixtures thereof, or the triphenylmethyl cation. Aluminoxanes or mixtures of aluminum-containing Lewis acids with water are particularly preferred. According to current knowledge, all the acids act as ionizing agents which form a metallocenium cation, the charge of which is compensated by a bulky, poorly coordinating anion.

According to the invention, the reaction products of such ionizing agents with metallocene compounds of the formula (I) or (XIII) can furthermore be employed. They can be described by the formulae (XIa) to (XId)

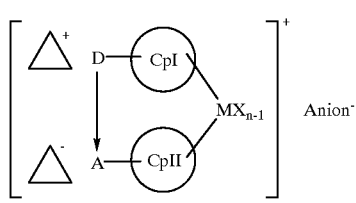

(XIa)

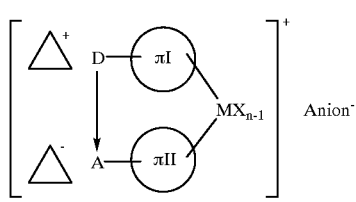

(XIb)

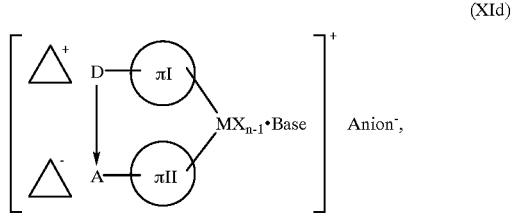

(XIc)

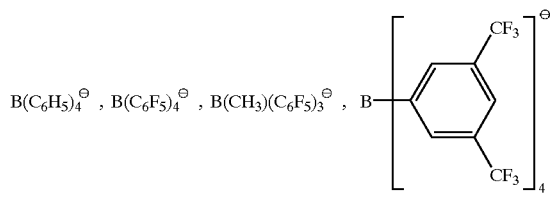

(XId)

in which
Anion represents the entire bulky, poorly coordinating anion and Base represents a Lewis base.

The metallocene compounds (I) and (XIII) which can be employed according to the invention can be present in monomeric, dimeric or oligormeric form.

Examples of poorly coordinating anions are, for example,

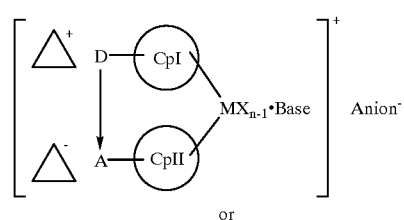

or sulfonates, such as tosylates or triflates, tetrafluoroborates, hexafluorophosphates or hexafluoroantimonates, perchlorates, and voluminous cluster molecular anions of the carborane type, for example $C_2B_9H_{12}^{\ominus}$ or $CB_{11}H_{12}^{\ominus}$. If such anions are present, metallocene compounds can also act as highly active polymerization catalysts in the absence of aluminoxane. This is the case, above all, if one X ligand represents an alkyl group, allyl or benzyl. However, it may also be advantageous to employ such metallocene complexes with voluminous anions in combination with aluminum-alkyls, such as $(CH_3)_3Al$, $(C_2H_5)_3Al$, (n-/i-propyl)$_3$Al, (n-/t-butyl)$_3$Al, (i-butyl)$_3$Al, the isomeric pentyl, hexyl or octyl aluminum-alkyls or lithium-alkyls, such as methyl-Li, benzyl-Li or butyl-Li, or the corresponding organo-Mg compounds, such as Grignard compounds, or organo-Zn compounds. Such metal-alkyls on the one hand transfer alkyl groups to the central metal, and on the other hand trap water or catalyst poisons from the reaction medium or monomer during polymerization reactions. Metal-alkyls of the type described can also advantageously be employed in combination with aluminoxane cocatalysts, for example in order to reduce the amount of aluminoxane required. Examples of boron compounds with which, when used, such anions are introduced are:
triethylammonium tetraphenylborate,
tripropylammonium tetraphenylborate,
tri(n-butyl)ammonium tetraphenylborate, tri(t-butyl)ammonium tetraphenylborate,
N,N-dimethylanilinium tetraphenylborate,
N,N-diethylanilinium tetraphenylborate,
N,N-dimethyl(2,4,6-trimethylanilinium) tetraphenylborate,
trimethylammoniumn tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl(2,4,5-tri-methylanilinium) tetrakis(pentafluorophenyl)borate,
trimethylammonium tetrakis(2,3,4,6-tetrafluorophenyl)borate,
triethylammonium tetrakis(2,3,4,6-tetrafluorophenyl)borate,
tripropylammonium tetrakis(2,3,4,6-tetrafluorophenyl)borate,
tri(n-butyl)ammonium tetrakis(2,3,4,6-tetrafluorophenyl)borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-dimethylanilinium tetrakis(2,3,4,6-tetrafluorophenyl)borate and
N,N-dimethyl(2,4,6-trimetrylanisinium) tetrakis(2,3,4,6-tetrafluorophenyl)borate;
dialkylammmonium salts, such as:
  di(i-propyl)ammonium tetrakis(pentafluorophenyl)borate and
  dicyclohexylammonium tetrakis(pentafluorophenyl)borate;
    tri-substituted phosphonium salts, such as:
      triphenyl phosphonium tetrakis(pentafluorophenyl)borate,
      tri(o-tolyl)phosphonium tetrakis(pentafluorophenyl)borate and
      tri(2,6-dimethylphenyl)phosphonium tetrakis(pentafluorophenyl)borate;
      tritolylmethyl tetrakis(pentafluorophenyl)borate,
      triphenylmethyl tetraphenylborate (trityl tetraphenylborate),
      trityl tetrakis(pentafluorophenyl)borate,
      silver tetrafluoroborate,
      tris(pentafluorophenyl)borane and
      tris(trifluoromethyl)borane.

The metallocene compounds to be employed according to the invention and the π complex compounds can be employed in isolated form as the pure substances for the (co)polymerization. However, it is also possible to produce them and use them "in situ" in the (co)polymerization reactor in a manner known to the expert.

The first and the second carbanion CpI and CpII having a cyclopentadienyl skeleton can be identical or different. The cyclopentadienyl skeleton can be, for example, one from the group consisting of cyclopentadiene, substituted cyclopentadiene, indene, substituted indene, fluorene and substituted fluorene. 1 to 4 substituents may be present per cyclopentadiene or fused-on benzene ring. These substituents can be $C_1$–$C_{20}$-alkyl, such as methyl, ethyl, propyl, isopropyl, butyl or iso-butyl, hexyl, octyl, decyl, dodecyl, hexadecyl, octadecyl or eicosyl, $C_1$–$C_{20}$-alkoxy, such as methoxy, ethoxy, propoxy, isopropoxy, butoxy or iso-butoxy, hexoxy, octyloxy, decyloxy, dodecyloxy, hexadecyloxy, octadecyloxy, eicosyloxy, halogen, such as fluorine, chlorine or bromine, $C_6$–$C_{12}$-aryl, such as phenyl, $C_1$–$C_4$-alkyl-phenyl, such as tolyl, ethylphenyl (i-) propylphenyl, (i-, tert-)butylphenyl or xylyl, halogenophenyl, such as fluoro-, chloro- or bromophenyl, naphthyl or biphenylyl, triorganyl-silyl, such as trimethylsilyl (TMS), ferrocenyl and D or A, as defined above. Fused-on aromatic rings can furthermore be partly or completely hydrogenated, so that only the double bond of which both the fused-on ring and the cyclopentadiene ring have a portion remains. Benzene rings, such as in indene or fluorene, can furthermore contain one or two further fused-on benzene rings. The cyclopentadiene or cyclopentadienyl ring and a fused-on benzene ring can also furthermore together contain a further fused-on benzene ring.

In the form of their anions, such cyclopentadiene skeletons are excellent ligands for transition metals, each cyclopentadienyl carbanion of the optionally substituted form mentioned compensating a positive charge of the central metal in the complex. Individual examples of such carbanions are cyclopentadienyl, methyl-cyclopentadienyl, 1,2-dimethyl-cyclopentadienyl, 1,3-dimethyl-cyclopentadienyl, indenyl, phenylindenyl, 1,2-diethyl-cyclopentadienyl, tetramethyl-cyclopentadienyl, ethyl-cyclopentadienyl, n-butyl-cyclopentadienyl, n-octyl-cyclopentadienyl, β-phenylpropyl-cyclopentadienyl, tetrahydroindenyl, propyl-cyclopentadienyl, t-butyl-cyclopentadienyl, benzyl-cyclopentadienyl, diphenylmethyl-cyclopentadienyl, trimethylgermyl-cyclopentadienyl, trimethylstannyl-cyclopentadienyl, trifluoromethyl-cyclopentadienyl, trimethylsilyl-cyclopentadienyl, pentamethylcyclopentadienyl, fluorenyl, tetrahydro- and octahydro-fluorenyl, fluorenyls and indenyls which are benzo-fused on the six-membered ring, N,N-dimethylamino-cyclopentadienyl, dimethylphosphino-cyclopentadienyl, methoxy-cyclopentadienyl, dimethylboranyl-cycl opentadienyl and (N,N-dimethylaminomethyl)-cyclopentadienyl.

In addition to the first donor-acceptor bond between D and A which is obligatorily present, further donor-acceptor bonds can be formed if additional D and/or A are present as substituents of the particular cyclopentadiene systems or substituents or parts of the π systems. All donor-acceptor bonds are characterized by their reversibility described above. In the case of several D and A, these can occupy various positions of those mentioned. The invention accordingly relates both to the bridged molecular states (Ia) and (XIIIa) and to the non-bridged state (Ib) and (XIIIb). The number of D groups can be identical to or different from the number of A groups. Preferably, CpI and CpII or πI and πII are linked via only one donor-acceptor bridge.

In addition to the D/A bridges according to the invention, covalent bridges can also be present. In this cases, the D/A bridges intensify the stereorigidity and the heat stability of the catalyst. By changing between the closed and open D/A bond, sequence polymers are accessible in the case of copolymers of different chemical composition.

The π complex compounds are likewise characterized by the presence of at least one coordinate bond between donor atom(s) D and acceptor atom(s) A. Both D and A here can be substituents of their particular π systems πI and πII or part of the π system, but always at least one of D and A is part of the π system. π system here is understood as meaning the entire π system, which is optionally fused once or twice. The following embodiments result from this:

D is part of the π system, A is a substituent of the π system;

D is a substituent of the π system, A is part of the π system;

D and A are parts of their particular π system.

The following heterocyclic ring systems in which D or A is part of the ring system may be mentioned as examples:

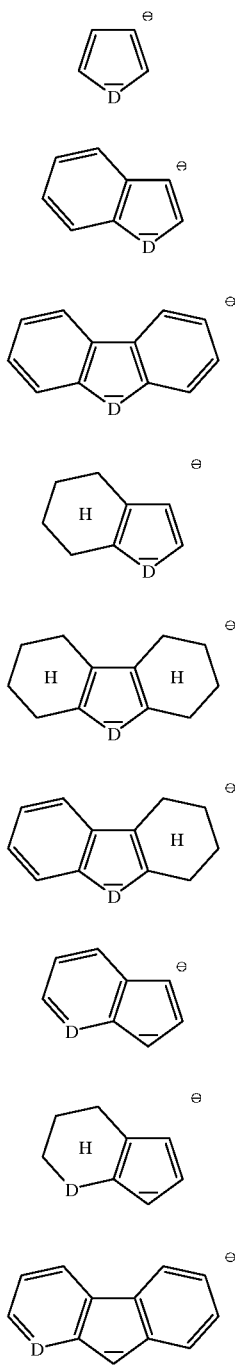

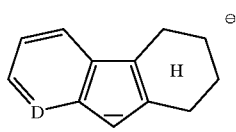

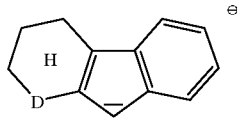

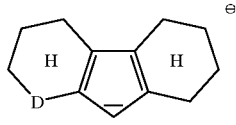

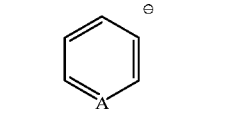

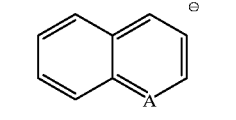

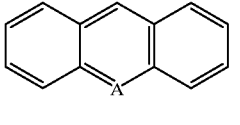

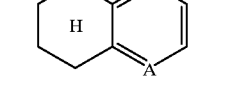

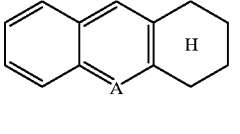

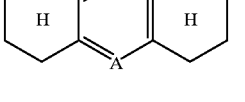

Important heterocyclic ring systems are the systems labelled (a), (b), (c), (d), (g), (m), (n) and (o); those labelled (a), (b), (c) and (m) are particularly important.

In the case where one of D and A is a substituent of an associated ring system, the ring system is 3-, 4-, 5-, 6-, 7- or 8-membered with or without an electric charge, and can be further substituted and/or fused in the manner described. 5- and 6-membered ring systems are preferred. The negatively charged cyclopentadienyl system is particularly preferred.

The first and the second π system πI and πII respectively, if it is formed as a ring system, can correspond to CpI and CpII respectively in the case where one of D and A is a substituent of the ring system.

Possible donor groups are, above all, those in which the donor atom D is an element of main group 5, 6 or 7, preferably 5 or 6, of the Periodic Table of the elements (Mendeleev) and has at least one free electron pair, and where the donor atom in the case of elements of main group 5 is in a bond state with substituents, and in the case of elements of main group 6 can be in such a state; donor atoms of main group 7 carry no substituents. This is illustrated by the example of phosphorus P, oxygen O and chlorine Cl as donor atoms as follows, where "subst." represents those substituents mentioned and "—Cp" represents the bond to the cyclopentadienyl-containing carbanion, a line with an arrow has the meaning of a coordinate bond given in formula (I) and other lines denote electron pairs present:

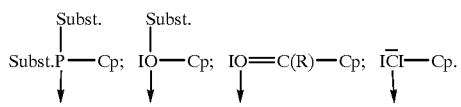

Possible acceptor groups are, above all, those in which the acceptor atom A is an element from main group 3 of the Periodic Table of the elements (Mendeleev), such as boron, aluminum, gallium, indium and thallium, is in a bond state with substituents and has an electron gap.

D and A are linked by a coordinate bond, where D assumes a positive (part) charge and A assumes a negative (part) charge.

A distinction is accordingly made between the donor atom D and the donor group and between the acceptor atom A and the acceptor group. The coordinate bond D→A is established between the donor atom D and the acceptor atom A. The donor group denotes the unit of the donor atom D, the substituent optionally present and the electron pairs present; the acceptor group correspondingly denotes the unit of the acceptor atom A, the substituent and the electron gap present.

The bond between the donor atom or the acceptor atom and the cyclopentadienyl-containing carbanions can be interrupted by spacer groups in the context of D-spacer-Cp or A-spacer-Cp. In the third of the above formula examples, =C(R)-represents such a spacer between O and Cp. Such spacer groups are, for example:

dimethylsilyl, diethysilyl, di-n-propylsilyl, diisopropylsilyl, di-n-butylsilyl, di-t-butylsilyl, di-n-hexylsilyl, methylphenylsilyl, ethylmethylsilyl, diphenylsilyl, di-(p-t-butylphenylsilyl), n-hexylmethylsilyl, cyclopentamethylenesilyl, cyclotetramethylenesilyl, cyclotrimethylenesilyl, dimethylgermanyl, diethylgermanyl, phenylamino, t-butylamino, methylamino, t-butylphosphino, ethylphosphino, phenylphosphino, methylene, dimethylmethylene (i-propylidene), diethylmethylene, ethylene, dimethylethylene, diethylethylene, dipropylethylene, propylene, dimethylpropylene, diethylpropylene, 1,1-dimethyl-3,3-dimethylpropylene, tetramethyldisiloxane, 1,1,4,4-tetramethyldisilylethylene, diphenylmethylene.

D and A are preferably bonded to the cyclopentadienyl-containing carbanion without a spacer.

D and A independently of one another can be on the cyclopentadiene (or -dienyl) ring or on a fused-on benzene ring or on another substituent of CpI and CpII respectively or πI and πII respectively. In the case of several D and A, these can occupy various positions of those mentioned.

Substituents on the donor atoms N, P, As, Sb, Bi, O, S, Se and Te and on the acceptor atoms B, Al, Ga, In and Tl are, for example: $C_1$–$C_{12}$(cyclo)alkyl, such as methyl, ethyl, propyl, i-propyl, cyclopropyl, butyl, i-butyl, tert-butyl, cyclobutyl, pentyl, neopentyl, cyclopentyl, hexyl, cyclohexyl and the isomeric heptyls, octyls, nonyls, decyls, undecyls and dodecyls; the $C_1$–$C_{12}$-alkoxy groups which correspond to these; vinyl, butenyl and aflyl; $C_6$–$C_{12}$-aryl, such as phenyl, naphthyl or biphenylyl and benzyl, which can be substituted by halogen, 1 or 2 $C_1$–$C_4$-alkyl groups, $C_1$–$C_4$-alkoxy groups, nitro or halogenoalkyl groups, $C_1$–$C_6$-alkyl-carboxyl, $C_1$–$C_6$-alkyl-carbonyl or cyano (for example perfluorophenyl, m,m'-bis(trifluoromethyl)-phenyl and analogous substituents familiar to the expert); analogous aryloxy groups; indenyl; halogen, such as F, Cl, Br and I, 1-thienyl, disubstituted amino, such as ($C_1$–$C_{12}$-alkyl)$_2$amino, and diphenylamino, tris-($C_1$–$C_{12}$-alkyl)-silyl, NaSO$_3$-aryt, such as NaSO$_3$-phenyl and NaSO$_3$-tolyl, and $C_6H_5$—C≡C—; aliphatic and aromatic $C_1$–$C_{20}$-silyl, the alkyl substituents of which can be octyl, decyl, dodecyl, stearyl or eicosyl, in addition to those mentioned above, and the aryl substituents of which can be phenyl, tolyl, xylyl, naphthyl or biphenylyl; and those substituted silyl groups which are bonded to the donor atom or the acceptor atom via —CH$_2$—, for example (CH$_3$)$_3$SiCH$_2$—; and ($C_1$–$C_{12}$-alkyl)(phenyl)amino, ($C_1$–$C_{12}$-alkylphenyl)$_2$amino, $C_6$–$C_{12}$-aryloxy with the abovementioned aryl groups, $C_1$–$C_8$-perfluoroalkyl and perfluorophenyl. Preferred substituents are: $C_1$–$C_6$-alkyl, $C_5$–$C_6$-cycloalkyl, phenyl, tolyl, $C_1$–$C_6$-alkoxy, $C_6$–$C_{12}$-aryloxy, vinyl, allyl, benzyl, perfluorophenyl, F, Cl, Br, di-($C_1$–$C_6$-alkyl)-amino and diphenylamino.

Donor groups are those in which the free electron pair is located on the N, P, As, Sb, Bi, O, S, Se, Te, F, Cl, Br and I; of these, N, P, O and S are preferred. Examples of donor groups which may be mentioned are: (CH$_3$)$_2$N—, (C$_2$H$_5$)$_2$N—, (C$_3$H$_7$)$_2$N—, (C$_4$H$_9$)$_2$N—, (C$_6$H$_5$)$_2$N—, (CH$_3$)$_2$P—, (C$_2$H$_5$)$_2$P—, (C$_3$H$_7$)$_2$P—, (i-C$_3$H$_7$)$_2$P—, (C$_4$H$_9$)$_2$P—, (t-C$_4$H$_9$)$_2$P—, (cyclohexyl)$_2$P—, (C$_6$H$_5$)$_2$P—, CH$_3$O—, CH$_3$S—, C$_6$H$_5$S—, —C(C$_6$H$_5$)=O, —C(CH$_3$)=O, —OSi(CH$_3$)$_3$ and —OSi(CH$_3$)$_2$-t-butyl, in which N and P each carry a free electron pair and O and S each carry two free electron pairs, and where in the last two examples mentioned, the double-bonded oxygen is bonded via a spacer group, and systems such as the pyrrolidone ring, where the ring members other than N also act as spacers.

Acceptor groups are those in which an electron pair gap is present on B, Al, Ga, In or Tl, preferably B or Al; examples which may be mentioned are (CH$_3$)$_2$B—, (C$_2$H$_5$)$_2$B—, H$_2$B—, (C$_6$H$_5$)$_2$B—, (CH$_3$)(C$_6$H$_5$)$_2$B—, (vinyl)$_2$B—, (benzyl)$_2$B—, Cl$_2$B—, (CH$_3$O)$_2$B—, Cl$_2$Al—, (CH$_3$)Al—, (i-C$_4$H$_9$)$_2$Al—, (Cl)(C$_2$H$_5$)$_2$Al—, (CH$_3$)$_2$Ga—, (C$_3$H$_7$)$_2$Ga—, ((CH$_3$)$_3$Si-CH$_2$)$_2$Ga—, (vinyl)$_2$Ga—, (C$_6$H$_5$)$_2$Ga—, (CH$_3$)$_2$In—, ((CH$_3$)$_3$Si—CH$_2$)$_2$In—, (cyclopentadienyl)$_2$In—.

Those donor and acceptor groups which contain chiral centers or in which 2 substituents form a ring with the D or A atoms are furthermore possible. Examples of these are, for example,

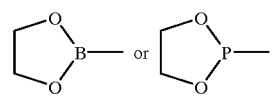

Preferred donor-acceptor bridges between CpI and CpII are, for example, the following:

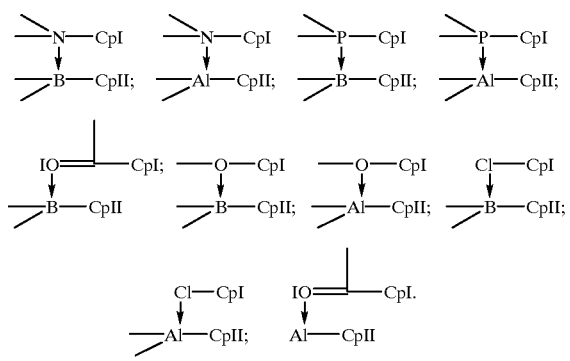

One or both π systems πI and/or πII can be present as a heterocyclic ring in the form of the above ring systems (a) to (r). D here is preferably an element of main group 5 or 6 of the Periodic Table of the Elements (Mendeleev); A here is preferably boron. Some examples of such hetero-π systems, in particular heterocyclic compounds, are:

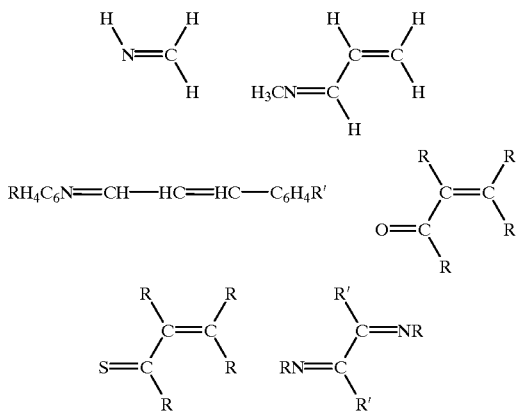

R and R'=H, alkyl, aryl or aralkyl, for example methyl, ethyl, t-butyl, phenyl or o,o'-di-(it-propyl)-phenyl.

Examples of heterocyclic radicals are: pyrrolyl, methylpyrrolyl, dimethylpyrrolyl, trimethylpyrrolyl, tetramethylpyrrolyl, t-butylpyrrolyl, di-t-butylpyrrolyl, indolyl, methylindolyl, dimethylindolyl, t-butylindolyl, di-t-butylindolyl, tetramethylphospholyl, tetraphenylphospholyl, triphenylphospholyl, trimethylphospholyl, phosphaindenyl, dibenzophospholyl (phosphafluorenyl) and dibenzopyrrolyl.

Preferred donor-acceptor bridges between πI and πII are, for example, the following: N→B, N→Al, P→B, P→Al, O→B, O→Al, Cl→B, Cl→Al, C=O→B and C=O→Al, where both atoms of these donor-acceptor bridges can be parts of a hetero-π system or one atom (donor or acceptor) is part of a π system and the other is a substituent of the second π system, or where both atoms are substituents of their particular ring and one of the rings additionally contains a heteroatom.

According to the above description, the two ligand systems πI and πII can be linked by one, two or three donor-acceptor bridges. This is possible since, according to the invention, formula (Ia) contains the D→A bridge described, but the ligand systems πI and πII can carry further D and A as substituents or hetero-π centers; the number of resulting additional D→A bridges is zero, one or two. The number of D and A substituents on πI and πII respectively can be identical or different. The two ligand systems πI and πII can additionally be bridged covalently. (Examples of covalent bridges are described above as spacer groups.) However, compounds without a covalent bridge, in which πI and πII accordingly are linked only via a donor-acceptor bridge, are preferred.

M represents a transition metal from sub-group 3, 4, 5 or 6 of the Periodic Table of the elements (Mendeleev), including the lanthanides and actinides; examples which may be mentioned are: Sc, Y, La, Sm, Nd, Lu, Ti, Zr, Hf. Th, V, Nb, Ta and Cr. Ti, Zr, Hf, V, Nb and Ta are preferred.

In the formation of the metallocene structure or π complex structure, in each case a positive charge of the transition metal M is compensated by in each case a cyclopentadienyl-containing carbanion. Positive charges which still remain on the central atom M are satisfied by further, usually monovalent anions X, two identical or different anions of which can also be linked to one another (dianions x x), for example monovalently or divalently negative radicals from identical or different, linear or branched, saturated or unsaturated hydrocarbons, amines, phosphines, thioalcohols, alcohols or phenols. Simple anions such as $Cr_3^-$, $NR_2^-$, $PR_2^-$, $OR^-$, $SR^-$ and the like can be bonded by saturated or unsaturated hydrocarbon or silane bridges, dianions being formed and it being possible for the number of bridge atoms to be 0, 1, 2, 3, 4, 5 or 6, 0 to 4 bridge atoms being preferred and 1 or 2 bridge atoms particularly preferred. The bridge atoms can also carry further hydrocarbon substituents R in addition to H atoms. Examples of bridges between the simple anions are, for example, $—CH_2—$, $—CH_2—CH_2—$, $—(CH_2)_3—$, $CH=CH$, $—(CH=CH)_2—$, $—CH=CH—CH_2—$, $CH_2—CH=CH—CH_2—$, $—Si(CH_3)_2—$ and $C(CH_3)_2—$. Examples of X are: hydride, chloride, methyl, ethyl, phenyl, fluoride, bromide, iodide, the n-propyl radical, the i-propyl radical, the n-butyl radical, the amyl radical, the i-amyl radical, the hexyl radical, the i-butyl radical, the heptyl radical, the octyl radical, the nonyl radical, the decyl radical, the cetyl radical, methoxy, ethoxy, propoxy, butoxy, phenoxy, dimethylamino, diethylamino, methylethylamine, di-t-butylamino, diphenylamino, diphenylphosphino, dicyclohexylphosphino, dimethylphosphino, methylidene, ethylidene, propylidene and the ethylene glycol dianion. Examples of dianions are 1,4-diphenyl-1,3-butadienediyl, 3-methyl-1,3-pentadienediyl, 1,4-dibenzyl-1,3-butadienediyl, 2,4-hexadienediyl, 1,3-pentadienediyl, 1,4-ditolyl-1,3-butadienediyl, 1,4-bis(trimethylsilyl)-1,3-butadienediyl and 1,3-butadienediyl. 1,4-Diphenyl-1,3-butadienediyl, 1,3-pentadienediyl, 1,4-dibenzyl-1,3-butadienediyl, 2,4-hexadienediyl, 3-methyl -1,3-pentadienediyl, 1,4-ditolyl-1,3-butadienediyl and 1,4-bis (trimethylsilyl)-1,3-butadienediyl are particularly preferred. Further examples of dianions are those with heteroatoms, for example of the structure

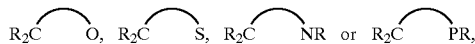

where the bridge has the meaning given. Weakly or non-coordinating anions of the abovementioned type are moreover particularly preferred for charge compensation.

The activation by such voluminous anions is effective, for example, by reaction of the D/A-π complex compounds, in particular the D/A-metallocenes, with tris (pentafluorophenyl)-borane, triphenylborane, triphenylaluminum, trityl tetrakis(pentafluorophenyl)-borate or N,N-dialkylphenylammonium tetrakis-(pentafluorophenyl-borate or the corresponding phosphonium or sulfonium salts of borates, or alkali metal or alkaline earth metal, thallium or silver salts of borates, carboranes, tosylates, triflates, perfluorocarboxylates, such as trifluoroacetate, or the corresponding acids. D/A-metallocenes in which the anion equivalent X represents alkyl, allyl, aryl or benzyl groups are preferably employed here. Such derivatives can also be prepared "in situ" by reacting D/A metallocenes with other anion equivalents, such as X=F, Cl, Br, OR and the like, beforehand with aluminum-alkyls, organolithium compounds or Grignard compounds or zinc- or lead-alkyls. The reaction products obtainable therefrom can be activated with abovementioned boranes or borates without prior isolation.

The index n assumes the value zero, one, two, three or four, preferably zero, one or two, depending on the charge of M. The abovementioned sub-group metals can in fact assume valencies/charges of two to six, preferably two to four, inter alia depending on which of the sub-groups they belong to, in each case two of these valencies/charges being compensated by the carbanions of the metallocene compound. In the case of $La^{3+}$, the index n accordingly assumes the value one, and in the case of $Zr^{4+}$ it assumes the value two; in the case of $Sm^{2+}$, n is zero.

To prepare the metallocene compounds of the formula (I), either in each case a compound of the above formulae (II) and (III) or in each case a compound of the above formulae (IV) and (V) or in each case a compound of the above formulae (VI) and (VII) or in each case a compound of the above formulae (VIII) and (III) or in each case a compound of the above formulae (IV) and (IX) or in each case a compound of the above formulae (X) and (VII) are reacted with one another, with elimination or splitting off of alkali metal-X, alkaline earth metal-$X_2$, silyl-X, germyl-X, stannyl-X or HX compounds, in an aprotic solvent at temperatures from −78° C. to +120° C., preferably from −40° C. to +70° C., and in a molar ratio of (II):(III) or (IV):(V) or (VI):(VII) or (VIII):(III) or (IV):(IX) or (X):(VII) of 1:0.5–2, preferably 1:0.8–1.2, particularly preferably 1:1. In the cases of reaction of (VIII) with (III) or (IV) with (IX) or (X) with (VII), it is possible to dispense with an aprotic solvent if (VIII), (IX) or (X) is liquid under the reaction conditions. Examples of such compounds eliminated or split off are: TlCl, LiCl, LiBr, LiF, LiI, NaCl, NaBr, KCl, KF, $MgCl_2$, $MgBr_2$, $CaCl_2$, $CaF_2$, trimethylchlorosilane, triethylchlorosilane, tri-(n-butyl)-chlorosilane, triphenylchlorosilane, trimethylchlorogermane, trimethylchlorostannane, dimethylamine, diethylamine, dibutylamine and other compounds which can be ascertained by the expert from the abovementioned substitution pattern.

Compounds of the formula (II) and (IV) are thus carbanions having a cyclopentadienyl skeleton or a heterocyclic skeleton which contains 1 to 3 donor groups, which are covalently bonded or incorporated as heterocyclic ring members and are used for the D/A bridge formation, and contain a cation as a counter-ion to the negative charge of the cyclopentadienyl skeleton. Compounds of the formula (VIII) are non-charged cyclic skeletons with likewise 1 to 3 donor groups used for D/A bridge formation, but with leaving groups $E(R^1R^2R^3)$ which can easily be split off, such as silyl, germyl or stannyl groups or hydrogen, instead of the ionic groups.

The second component for forming the metallocene compounds to be employed according to the invention, that is to say the compound of the formula (III) or (V), is likewise a carbanion having a cyclopentadienyl skeleton which is identical to the cyclopentadienyl skeleton of the compound (II) or (IV) or different from this, but carries 1 to 3 acceptor groups instead of the donor groups. In a corresponding manner, compounds of the formula (IV) are uncharged cyclopentadiene skeletons having 1 to 3 acceptor groups and likewise leaving groups $F(R^4R^5R^6)$ which can easily be split off.

In a completely analogous manner, compounds of the formulae (VI) or (X) are starting substances with a preformed D→A bond which are carbanion-counter-cation compounds or uncharged cyclopentadiene structures with 1 to 3 D→A bonds possible in total and give the metallocene compounds (I) by reaction with compounds of the formula (VII).

The two starting substances of the preparation process, that is to say (II) and (III) or (IV) and (V) or (VI) and (VII) or (VIII) and (III) or (IV) and (IX) or (X) and (VII) react spontaneously when brought together, with simultaneous formation of the donor-acceptor group D→A— or complexing of the metal cation M with elimination of M'X or $E(R^1R^2R^3)X$ or $F(R^4R^5R^6)X$ or HX. In the description of the donor-acceptor group, the substituents on D and A have been omitted for clarity. M' is one cation equivalent of an alkali metal or alkaline earth metal, such as Li, Na, K, ½Mg, ½C, ½Sr, ½Ba or thallium.

The compounds of the formula (XIIIa+b) are prepared analogously in the above-mentioned manner.

Solvents for the preparation process are aprotic, polar or non-polar solvents, such as aliphatic and aromatic hydrocarbons or aliphatic and aromatic halogeno hydrocarbons. Other aprotic solvents such as are known to the expert are also possible in principle, but because of the easier working up, those with boiling points which are too high are less preferred. Typical examples are: n-hexane, cyclohexane, pentane, heptane, petroleum ether, toluene, benzene, chlorobenzene, methylene chloride, diethyl ether, tetrahydrofuran and ethylene glycol dimethyl ether.

The starting substances of the formulae (II), (III), (IV) and (V) can be prepared by processes known from the literature or analogously to these. Thus, for example, trimethylsilylcyclopentadiene, which is available on the market, can be reacted first with butyl-lithium and then with trimethylsilyl fluoride to give bis(trimethylsilyl)-cyclopentadiene analogously to J. of Organometallic Chem. (1971), 29, 227. This product can in turn be reacted with boron trichloride to give trimethylsilylcyclopentadienyl-dichloroborane (analogously to J. of Organometallic Chem. (1979), 169, 327), which finally can be reacted with titanium tetrachloride analogously to J. of Organometallic Chem. (1979), 169, 373 to give dichloroborylcyclopentadienyl-titanium trichloride. This compound mentioned last is already a prototype of the compounds of the formula (III); the compound mentioned last can furthermore be reacted selectively with trimethylaluminum, the two chlorine atoms bonded to the boron atom being replaced by methyl groups, a further compound of the formula (III) being demonstrated. Cyclopentadienyl-thallium, which is available on the market, can be reacted with chloro-diphenylphosphine and further with butyl-lithium analogously to the process descriptions in J. Am. Chem. Soc. (1983) 105, 3882 and Organometallics (1982) 1, 1591, a prototype of the compounds of the formula (II) being obtained. The formation of dimethylstannyl-diphenylphosphine-indene by reaction of indene first with butyl-lithium, as already mentioned above, and then with chlorodiphenylphosphine may be mentioned as a further example; further reactions, first again with butyl-lithium and then with chlorotributyltin, gives the compound mentioned, which, after further reaction with zirconium tetrachloride, gives diphenylphosphino-indenyl-zirconium trichloride as a representative of compounds of the formula (IV). Such syntheses and preparation procedures are familiar to the expert operating in the field of organometallic and organoelemental chemistry and are published in numerous literature references, of which only a few are given by way of example above.

$10^1$ to $10^{12}$ mol of comonomers are reacted per mole of π complex compounds or metallocene compounds. The π complex compounds or metallocene compounds can be employed together with cocatalysts. The ratio of the amounts between the metallocene compound or π complex compound and cocatalyst is 1 to 100,000 mol of cocatalyst per mole of metallocene π complex compound. Cocatalysts are understood as meaning, for example, aluminoxane compounds. These are understood as meaning those of the formula

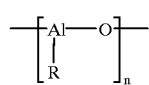

(XII)

in which

R represents $C_1$–$C_{20}$-alkyl, $C_6$–$C_{12}$-aryl or benzyl and n denotes a number from 2 to 50, preferably 10 to 35.

It is also possible to employ a mixture of various aluminoxanes or a mixture of precursors thereof (aluminumalkyls) in combination with water (in gaseous, liquid, solid or bonded form, for example as water of crystallization). The water can also be fed in as (residual) moisture of the polymerization medium, of the monomer or of a support, such as silica gel.

The bonds projecting from the square brackets of formula (XI) contain R groups or $AlR_2$ groups as end groups of the oligomeric aluminoxane. Such aluminoxanes are as a rule present as a mixture of several of them of different chain lengths. Fine analysis has also shown aluminoxanes with a cyclic or cage-like structure. Aluminoxanes are compounds which are available on the market. In the specific case of R=$CH_3$, methylaluminoxanes (MAO) are referred to.

Further cocatalysts are aluminum-alkyls, lithium-alkyls or organo-Mg compounds, such as Grignard compounds, or partly hydrolyzed organoboron compounds. Preferred cocatalysts are aluminoxanes.

The activation with the cocatalysts or the production of the voluminous non- or weakly coordinating anions can be carried out in an autoclave or in a separate reaction vessel (preforming). The activation can be carried out in the presence or absence of the monomer(s) to be polymerized. The activation can be carried out in an aliphatic or aromatic or halogenated solvent or suspending agent.

The π complex compounds or the metallocene compounds and the aluminoxanes can be employed both as such in homogeneous form and individually or together in heterogeneous form on supports. The support material here can be inorganic or organic in nature, such as silica gel, $Al_2O_3$, $MgCl_2$, NaCl, cellulose derivatives, starch and polymers. It is possible here both to apply first the π complex compound or the metallocene compound and to apply first the aluminoxane to the support, and then to add the other particular component. However, it is also equally possible to activate the metallocene compounds in homogeneous or heterogeneous form with the aluminoxane and then to apply the activated metallocene compound to the support.

Support materials are preferably pretreated by heat and/or chemicals in order to adjust the water content or the OH group concentration to a defined value or to keep it as low as possible. A chemical pretreatment can comprise, for example, reaction of the support with aluminum-alkyl. Inorganic supports are usually heated at 100° C. to 1000° C. for 1 to 100 hours before use. The surface area of such inorganic supports, in particular of silica ($SiO_2$), is between 10 and 1000 $m^2$/g, preferably between 100 and 800 $m^2$/g. The particle diameter is between 0.1 and 500 micrometers ($\mu$), preferably between 10 and 200$\mu$.

Cyclic monomers are mono- or polycyclic and fall under one of the two formulae

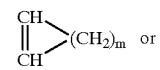

(XIV)

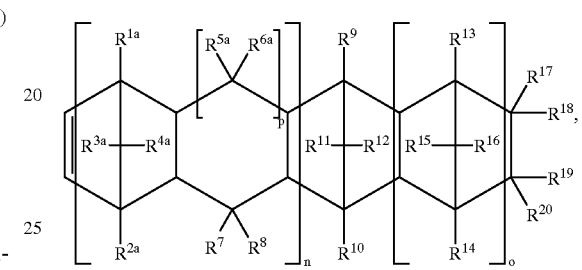

(XV)

in which the indices m denotes a number from 2 to 10, preferably 3 to 6, n denotes the number 0 or 1, o denotes the number 0, 1, 2 or 3 and p denotes the number 0 or 1, in formula (XIV) two adjacent $CH_2$ groups can be replaced by the group —CH=CH—, and in formula (XV) the radicals $R^{1a}$ to $R^{6a}$ and $R^7$ to $R^{20}$ independently of one another represent hydrogen, fluorine, chlorine, bromine, straight-chain or branched $C_1$–$C_{20}$-alkyl, $C_3$–$C_8$-cycloalkyl or $C_6$–$C_{16}$-aryl, where the radical pair $R^{18}/R^{19}$ can additionally denote a double bond or one of the groups —$CHR^{21}$—$CHR^{22}$—$CHR^{23}$—, —$CHR^{21}$—$CHR^{22}$—$CHR^{23}$—$CHR^{24}$— or —$CHR^{21}$—$CHR^{22}$—$CHR^{23}$—$CHR^{24}$—$CHR^{25}$—, in which $R^{21}$ to $R^{25}$ are hydrogen or $C_1$–$C_4$-alkyl, and the radical pair $R^{17}/R^{18}$ can additionally denote the double-bonded group =C($R^{26}$,$R^{27}$), in which $R^{26}$ and $R^{27}$ are $C_1$–$C_4$-alkyl, and $R^{27}$ can also be hydrogen.

Such cyclic monomers have one or more, preferably one or two double bonds, and are known and are employed, for example, in processes of EP-A 610 852, EP-A 690 078 and U.S. Pat. No. 5,567,777.

Preferred cyclic monomers of the formula (XV) are those of the formulae

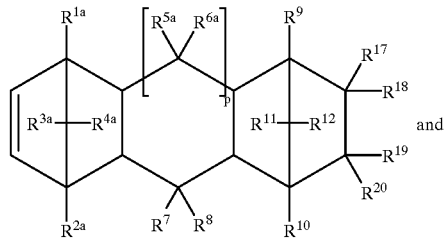

(XVa)

and

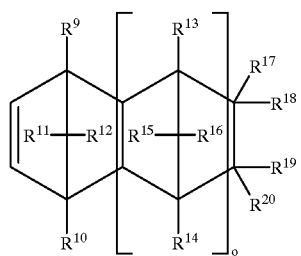

(XVb)

A non-exhaustive list of such cyclic comonomers given by way of example include cyclobutene, cyclopentene, cyclopentadiene, cyclohexene, cycloheptene, cyclooctene, cyclodecene, cyclododecene, bicyclo-2-heptene, tricyclo-3-decenes, tricyclo-3-undecenes, tetracyclo-3-dodecenes, pentacyclo-4-pentadecenes, pentacyclopentadecadienes, pentacyclo-3-pentadecenes, pentacyclo-4-hexadecenes, pentacyclo-3-hexadecenes, hexacyclo-4-heptadecenes, heptacyclo-5-eicosenes, heptacyclo-4-eicosenes, heptacyclo-5-heneicosenes, octacyclo-5-docosenes, nonacyclo-5-pentacosenes, nonacyclo-6-hexacosenes, cyclopentadiene/acenaphthylene adducts, 1,4-methano-1.4.4a.9a-tetrahydrofluorenes and 1,4-methano-1.4.4a.5.10.10a-hexahydroanthracenes, such as, for example, bicyclo[2,2,1]-hept-2-ene (norbornene), norbornadiene, 5-methyl-norbornene, 6-methylnorbornene, 5,6-dimethyl-norbornene, 1-methyl-norbornene, 5-isobutyl-norbornene, 7-methyl-norbornene, tricyclo[4,3,0,1$^{2,5}$]-3-decene, (5,6-trimethylene-norbornene), tricyclo[4,4,0,1$^{2,5}$]-3-undecene(5,6-tetramethylene-norbornene), 10-methyl-tricyclo[4,4,0,1$^{2,5}$]-3-undecene, 6-ethylbicyclo-[2.2.1]hept-2-ene, 6-n-butylbicyclo-[2.2.1]hept-2-ene, 6-isobutylbicyclo[2.2.1]hept-2-ene, 2-methyltricyclo[4.3.0.1$^{2,5}$]-3-decene, 5-methyltricyclo[4.3.0.1$^{2,5}$]-3-decene, tricyclo-[4.3.0.1$^{2,5}$]-3-undecene, tricyclo[4,3,0,1$^{2,5}$]-3,7-decadiene (dicyclopentadiene), tricyclo[4,3,0,1$^{2,5}$]-3-decene, tetracyclo[4,4,0,1$^{2,5}$,1$^{7,10}$]-3-dodecene, 8-methyl-tetracyclo[4,4,0,1$^{2,5}$,1$^{7,10}$]-3-dodecene, 8-cyclohexyl-tetracyclo[4,4,0,1$^{2,5}$,1$^{7,10}$]-3-dodecene, 8-stearyl-tetracyclo[4,4,0,1$^{2,5}$,1$^{7,10}$]-3-dodecene, the 5,10-dimethyl, 2,10-dimethyl, 8,9-dimethyl, 11,12-dimethyl, 2,7,9-trimethyl, 9-isobutyl, 11,12-dimethyl, 8-ethylidene-9-methyl, 8-chloro, 8-bromo or 8-fluoro derivative of tetracyclo[4,4,0,1$^{2,5}$,1$^{7,10}$]-3-dodecene, 8-ethyltetracyclo[4.4.0.1$^{2,5}$ $^{7,10}$]-3-dodecene, 8-propyltetracyclo[4.4.0.1$^{2,5}$.1$^{7,10}$]-3-dodecene, 8-butyltetracyclo[4.4.0.1$^{2,5}$,1$^{7,10}$]-3-dodecene, 8-isobutyl-tetracyclo[4.4.0.1$^{2,5}$.1$^{7,10}$]-3-dodecene, 8-hexyltetracyclo[4.4.0.1$^{2,5}$.1$^{7,10}$]-3-dodecene, 8-methyl-9-ethyltetracyclo[4.4.0.1$^{2,5}$.1$^{7,10}$]-3-dodecene, 9-ethyl-2,7-dimethyltetracyclo[4.4.0.1$^{2,5}$.1$^{7,10}$]-3-dodecene, 9-isobutyl-2,7-dimethyltetracyclo[4.4.0.1$^{2,5}$.1$^{7,10}$]-3-dodecene, 9,11,12-trimethyltetracyclo[4.4.0.1$^{2,5}$.1$^{7,10}$]-3-dodecene, 9-ethyl-11,12-di-methyl-tetracyclo[4.4.0.1$^{2,5}$.1$^{7,10}$]-3-dodecene, 9-isobutyl-11,12-dimethyl[4.4.0.1$^{2,5}$.1$^{7,10}$]-3-dodecene, 5,8,9,10-tetramethylcyclo[4.4.0.1$^{2,5}$.1$^{7,10}$]-3-dodecene, 8-ethylidene-tetracyclo[4.4.0.1$^{2,5}$.1$^{7,10}$]-3-dodecene, 8-ethylidene-9-methyltetracyclo[4.4.0.1$^{2,5}$.1$^{7,10}$]-3-dodecene, 8-ethylidene-9-ethyltetracyclo[4.4.0.1$^{2,5}$.1$^{7,10}$]-3-dodecene, 8-ethylidene-9-isopropyltetracyclo[4.4.0.1$^{2,5}$.1$^{7,10}$]-3-dodecene, 8-ethylidene-8-butyl-tetracyclo[4.4.0.1$^{2,5}$.1$^{7,10}$]-3-dodecene, 8-n-propylidenetetracyclo[4.4.0.1$^{2,5}$.1$^{7,10}$]-3dodecene, 8-n-propylidene-9-methyltetracyclo-[4.4.0.1$^{2,5}$.1$^{7,10}$]-3-dodecene, 8-n-propylidene-9-ethyltetracyclo[4.4.0.1$^{2,5}$.1$^{7,10}$]-3-dodecene, 8-n-propylidene-9-isopropyltetracyclo[4.4.0.1$^{2,5}$.1$^{7,10}$]-3-dodecene, 8-n-propylidene-9-butyltetracyclo[4.4.0.1$^{2,5}$.1$^{7,10}$]-3-dodecene, 8-isopropylidenetetracyclo[4.4.0.1$^{2,5}$.1$^{7,10}$]-3-dodecene, 8-isopropylidene-9-methyltetracyclo-[4.4.0.1$^{2,5}$.1$^{7,10}$]-3-dodecene, 8-iso-propylidene-9-ethyltetracyclo[4.4.0.1$^{2,5}$.1$^{7,10}$]-3-dodecene, 8-isopropylidene-9-isopropyltetracyclo[4.4.0.1$^{2,5}$.1$^{7,10}$]-3-dodecene, 8-isopropylidene-9-butyltetracyclo[4.4.0.1$^{2,5}$.1$^{7,10}$]-3-dodecene, 8,9-dichlorotetracyclo[4.4.0.1$^{2,5}$.1$^{7,10}$]-3-dodecene, pentacyclo[6,5,1,1$^{3,6}$0$^{2,7}$,0$^{9,13}$]-4-pentadecene, pentacyclo[7,4,0,1$^{2,5}$,1$^{9,12}$,0$^{8,13}$]-3-pentadecene, pentacyclo[8,4,0,1$^{2,5}$,1$^{9,12}$,0$^{8,13}$]-3-hexadecene, 1,3-dimethylpentacyclo[6.5.1.1$^{3,6}$.0$^{2,7}$.0$^{9,13}$]-4-pentadecene, 1,6-dimethyl[6.5.1.1$^{3,6}$.0$^{2,7}$.0$^{9,13}$]-4-pentadecene, 1,4,15-dimethyl[6.5.1.1$^{3,6}$.0$^{2,7}$.0$^{9,13}$]-4-pentadecene, pentacyclo[7.4.0.1$^{2,5}$.1$^{9,12}$.0$^{8,13}$]-3-pentadecene, methyl-substituted pentacyclo[7.4.0.1$^{2,5}$.1$^{9,12}$.0$^{8,13}$]-3-pentadecene, pentacyclo[6.5.1.1$^{3,6-}$.0$^{2,7}$.0$^{9,13}$]-4-pentadecene, 11-methylpentacyclo[8.4.0.1$^{2,5}$.1$^{9,12}$.0$^{8,13}$]-3-hexadecene, 11-ethyl-[8.4.0.1$^{2,5}$.1$^{9,12}$.0$^{8,13}$]-3-hexadecene, 10,11-dimethyl[8.4.0.1$^{2,5}$.1$^{9,12}$.0$^{8,13}$]-3-decene, pentacyclo[6.6.1.1$^{3,6}$.0$^{2,7}$.0$^{9,14}$]-4-hexadecene, 1,3-dimethylpentacyclo[6.6.1.1$^{3,6}$.0$^{2,7}$.0$^{9,14}$]-4-hexadecene, 15,16-dimethylpentacyclo[6.6.1.1$^{3,6}$.0$^{2,7}$.0$^{9,14}$]-4-hexadecene, hexacyclo[6,6,1,1$^{3,6}$,1$^{10,13}$,0$^{2,7}$,0$^{9,14}$]-heptadecene, heptacyclo[8,7,0,1$^{2,9}$,1$^{4,7}$,1$^{11,17}$,0$^{3,8}$0$^{12,16}$]-5-eicosene, heptacyclo[8,8,0,1$^{4,7}$,1$^{11,18}$,1$^{13,16}$,0$^{3,8}$,0$^{12,17}$]-5-heneicosene, 12-methyl-hexacyclo[6.6.1.1$^{3,6}$.1$^{10,13}$.0$^{2,7}$.0$^{9,14}$]-4-heptadecene, 12-ethylhexacyclo[6.6.1.1$^{3,6}$.1$^{10,13}$.0$^{2,7}$.0$^{9,14}$]-4-heptadecene, 2-isobutylhexacyclo[6.6.1.1$^{3,6}$.1$^{10,13}$.0$^{2,7}$.0$^{9,14}$]-4-heptadecene, 1,6,10-trimethylhexacyclo[6.6.1.1$^{3,6}$.1$^{10,13}$.0$^{2,7}$.0$^{9,14}$]-4-heptadecene, heptacyclo[8.7.0.1$^{3,6}$.1$^{10,17}$.1$^{12,15}$.0$^{2,7}$.0$^{11,16}$]-4-eicosene and its dimethyl-substituted derivatives, heptacyclo[8.8.0.1$^{4,7}$.1$^{11,18}$.1$^{13,16}$.0$^{3,8}$.0$^{12,17}$]-5-heneicosene and its trimethylsubstituted derivatives, 15-methylheptacyclo[8.8.0.1$^{4,7}$.1$^{11,18}$.1$^{13,16}$.0$^{3,8}$.0$^{12,17}$]-5-heneicosene, 5-phenyl-bicyclo[2.2.1]hept-2-ene, 5-methyl-5-phenyl-bicyclo[2.2.1]hept-2-ene, 5-benzylbicyclo[2.2.1]hept-2-ene, 5-tolyl-bicyclo[2.2.1]hept-2-ene, 2-(ethylphenyl)-bicyclo[2.2.1]hept-2-ene, 5-(isopropylphenyl)-bicyclo[2.2.1]hept-2-ene, 5-biphenyl-bicyclo[2.2.1]hept-2-ene, 5-(β-naphthyl)-bicyclo-[2.2.1]hept-2-ene, 5-(α-naphthyl)-bicyclo[2.2.1]hept-2-ene, 5-(anthracenyl)-bicyclo-[2.2.1]hept-2-ene, 5,6-diphenyl-bicyclo[2.2.1]hept-2-ene, 1,4-methano-1.4.4a.9a-tetrahydrofluorene, 1,4-methano-1.4.4a.5.10.10a-hexahydroanthracene, 8-phenyltetracyclo[4.4.0.1$^{2,5}$.1$^{7,10}$]-3-dodecene, 8-methyl-8-phenyl-tetracyclo[4.4.0.1$^{2,5}$.1$^{7,10}$]-3-dodecene, 8-benzyl-tetracyclo[4.4.0.1$^{2,5}$.1$^{7,10}$]-3-dodecene, 8-tolyl-tetracyclo[4.4.0.1$^{2,5}$.1$^{7,10}$]-3-dodecene, 8-(ethylphenyl)-tetracyclo[4.4.0.1$^{2,5}$.1$^{7,10}$]-3-dodecene, 8-(isopropylphenyl)-tetracyclo[4.4.0.1$^{2,5}$.1$^{7,10}$]-3-dodecene, 8,9-diphenyl-tetracyclo[4.4.0.1$^{2,5}$.1$^{7,10}$]-3-dodecene, 8-(biphenyl)-tetra-cyclo[4.4.0.1$^{2,5}$.1$^{7,10}$]-3-dodecene, 8-(β-naphthyl)-tetracyclo[4.4.0.1$^{2,5}$.1$^{7,10}$]-3-dodecene, 8-(α-naphthyl)-tetracyclo[4.4.0.1$^{2,5}$.1$^{7,10}$]-3-dodecene and 8-(anthracenyl)-tetracyclo[4.4.0.1$^{2,5}$.1$^{7,10}$]-3-dodecene.

Preferred cycloolefins are also those which are substituted, preferably once to three times per molecule, by halogen, —CF$_3$, —N(C$_1$–C$_8$-alkyl)$_2$, —CN, C$_1$–C$_{12}$-alkoxy or C$_1$–C$_{20}$-alkylene-COOC$_1$–C$_{20}$-alkyl.

The cycloolefins can also be polymerized in the presence of acyclic mono- or diolefins, alkines and carbon monoxide. Suitable acyclic olefins include C$_2$–C$_{40}$-α-olefins and C$_4$–C$_{24}$-diolefins, such as, for example, ethylene, propylene, 1-butene, 1-pentene, 1-hexene, 3-methyl-1-butene, 3-methyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene, 1-eicosene and mixtures of these α-olefins, as well as 1,3-butadiene, isoprene, 1,3-pentadiene, 1,4-hexadiene, 1,5-hexadiene, 1,6-heptadiene, 1,6- and 1,7-octadiene, 1,8-nonadiene, 1,9-decadiene, 1,11-dodecadiene, 1,19-eicodiene and mixtures of these diolefins. Mixtures of α-olefins and diolefins are also suitable.

Such olefins and diolefins can furthermore be substituted, for example by phenyl, substituted phenyl, haloen, the esterified carboxyl groups or the acid anhydride groups; compounds of this type are, for example, chloroprene, styrene, methylstyrene, chlorostyrene, fluorostyrene, indene, 4-vinyl-biphenyl, vinyl-fluorene, vinylanthracene, methyl methacrylate, ethyl acrylate, vinylsilane, trimethylallylsilane, vinyl chloride, vinylidene chloride, tetrafluoroethylene, isobutylene, vinyl-carbazole, vinylpyrrolidone, acrylonitrile, vinyl ethers and vinyl esters. Ring-opening polyadditions, for example of lactones, such as ε-caprolactone or δ-valerolactone, or of lactams, such as ε-caprolactam, are furthermore possible according to the invention. Preferred monomers are: ethylene, propylene, butene, hexene, octene, 1,5-hexadiene, 1,6-octadiene, methyl methacrylate, ε-caprolactone, δ-valerolactone and acetylene.

Ethylene and propylene are preferred.

The cyclic monomer of the formula (XIV) or (XV) is a molar proportion of 1 to 100% of the total number of moles of all the comonomers employed. The α-olefin is a molar proportion of 99 to 0% of the total number of moles of all the comonomers employed. The preferred amounts of cycloolefin to olefin are 20:80 mol % to 80:20 mol %. In the case where cycloolefins both of the formula (XIV) and of the formula (XV) are employed, the molar ratio thereof is 10:90 mol % to 90:10 mol %.

The process according to the invention is carried out at the abovementioned temperatures and pressures in the gas, bulk, liquid or in the slurry phase, depending on whether a soluble or an insoluble catalyst of the type described above is employed. The liquid phase or the slurry phase can be formed from the comonomers alone, i.e. without the use of an additional solvent. In the case where a solvent is used also, possible solvents for this are inert solvents, for example aliphatic or cycloaliphatic hydrocarbons, benzine or diesel oil fractions (if appropriate after hydrogenation), toluene, chlorobenzene, o-dichlorobenzene or chloronaphthalene. In solvents with a low boiling point, it can be ensured that the liquid phase is maintained by applying an adequate reaction pressure; these relationships are known to the expert. The polymers can be precipitated or reprecipitated by a non-solvent, such as methanol, and then dried.

Such (co)polymerizations are known and familiar to the expert. It is an advantage of the π complex compounds and metallocene compounds according to the invention that, by choosing the substituents, they can be prepared both as soluble π complex compounds or metallocene compounds optionally applied to supports, and as insoluble π complex compounds or metallocene compounds. Soluble π complex compounds or metallocene compounds will be employed, for example, for the solution process; heterogeneous metallocene compounds will be employed, for example, in the gas phase. According to the invention, the reaction can be carried out discontinuously or, preferably, continuously using one or more reactors or reaction zones. In the case of several reactors or reaction zones, different polymerization conditions can be established.

The π complex compounds, in particular the metallocene compounds, to be employed according to the invention allow, due to the donor-acceptor bridge, a defined opening of the two cyclopentadienyl skeletons like a beak, a controlled selectivity, a controlled molecular weight distribution and uniform incorporation of comonomers being ensured, in addition to a high activity. As a result of a defined beak-like opening, there is also space for voluminous monomers. The high uniformity in molecular weight distribution is furthermore optionally made possible from the uniform and defined site of the polymerization which takes place by insertion (single site catalyst) and can be adjusted by the choice of polymerization temperature.

The molecular weight distribution can be modified (broadened) in a controlled manner by employing several D/A catalysts simultaneously, in order to establish a certain profile of properties of the material. Accordingly, it is also possible to employ one or more D/A catalysts in combination with other metallocenes which have no D/A bridge.

The D/A structure can have the effect of extra-stabilizing the catalysts up to high temperatures, so that the catalysts can also be employed in the high temperature range. The possible thermal dissociation of the donor-acceptor bond is reversible and, as a result of this self-organization process and self-repair mechanism, leads to particularly high-quality catalyst properties.

Another valuable property of the D/A-π complex compounds, for example D/A-metallocene compounds, according to the invention is the possibility of self-activation and therefore of dispensing with expensive catalysts, in particular in the case of dianionic xx derivatives.

In this case, the acceptor atom A in the open form of the D/A-π complex compounds, for example D/A-metallocene compound, binds an x ligand, for example one side of a dianion, to form a zwitter-ionic metallocene structure, and thus generates a positive charge in the transition metal, while the acceptor atom A assumes a negative charge. Such a self-activation can be intramolecular or intermolecular. This may be illustrated by the example of the preferred linkage of two X ligands to a chelate ligand, that is to say of the butadienediyl derivative:

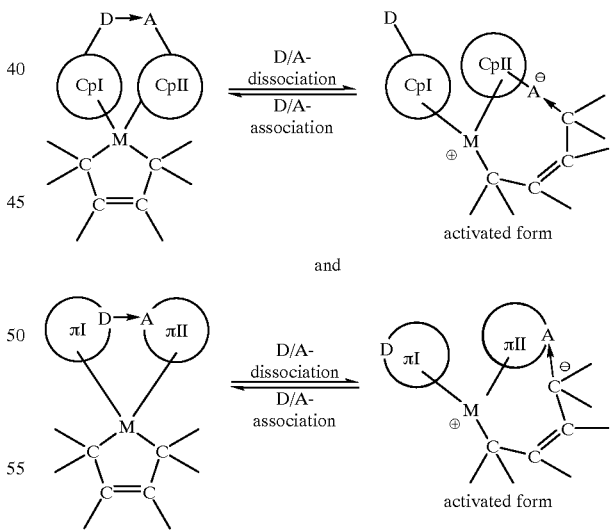

The bonding site between the transition metal M and H or substituted or unsubstituted C, in the formula example the still bonded substituted C of the butadienediyl dianion shown, is then the site for the olefin insertion for the polymerization.

Examples

All the reactions were carried out under strictly anaerobic conditions using Schlenk techniques or the high vacuum technique. The solvents used were dry and saturated with argon. Chemical shifts are stated in ppm, relative to the particular standard: $^1$H(tetramethylsilane), $^{13}$C (tetramethylsilane), $^{31}$P(85% strength $H_3PO_4$), $^{11}$B(boron trifluoride-etherate-18.1 ppm). Negative signs denote a shift to a higher field.

Example 1

Bis-(trimethylsilyl)-cyclopentadiene, Compound 1

14.7 g (0.106 mol) of trimethylsilyl-cyclopentadiene (obtained from Fluka) and 150 ml of tetrahydrofuran (THF) were introduced into a reaction flask and cooled to 0° C. 47.4 ml of a solution of butyl-lithium in n-hexane (2.3 molar; total aiamount 0.109 mol) were added dropwise in the course of 20 minutes. When the addition was complete, the yellow solution was stirred for a further hour; thereafter, the cooling bath was removed. The solution was stirred for a further hour at room temperature and then cooled to −20° C. 14.8 ml (0.117 mol) of trimethylsilyl chloride were then added dropwise in the course of 10 minutes and the reaction mixture was stirred at −10° C. for two hours. Thereafter, the cooling bath was removed and the reaction solution was warmed to room temperature and subsequently stirred for a further hour. The reaction mixture was filtered through Celite; the filter was washed with hexane and the hexane was removed from the combined filtrates in vacuo. On distillation at 26° C. under 0.4 mbar, the crude product gave 19 g of pure product of the compound 1 (85% of the theoretical yield). The boiling point and NMR data correspond to the literature data (J. Organometallic Chem. 29 (1971), 227; ibid. 30 (1971), C 57; J. Am. Chem. Soc. 102, (1980), 4429; J. Gen. Chem. USSR, English translation 43 (1973), 1970; J. Chem. Soc., Dalton Trans. 1980, 1156)

$^1$H-NMR (400 MHz, $C_6D_6$): δ=6.74 (m, 2H), 6.43 (m, 2H), −0.04 (s, 18H).

Example 2

Trimethylsilyl-cyclopentadienyl-dichloroborane, Compound 2

16 g (0.076 mol) of the compound 1 were introduced into a round-bottomed flask equipped with a dry ice cooling bath. 8.9 g (0.076 mol) of $BCl_3$ were condensed at −78° C. in a Schlenk tube and then added dropwise to the round-bottomed flask over a period of 5 minutes. The reaction mixture was warmed slowly to room temperature in the course of 1 hour and then kept at 55 to 60° C. for a further 2 hours. All the volatile compounds were removed in vacuo (3 mm Hg=4 mbar). Subsequent distillation at 39° C. under 0.012 mbar gave 14.1 g of the compound 2 (85% of the theoretical yield). The $^1$H-NMR agrees with the literature data and showed that a number of isomers had been prepared (cf. J. Organometallic Clhem. 169 (1979), 327). $^{11}$B-NMR (64.2 MHz, $C_6D_6$): δ=+31.5.

Example 3

Tributylstannyl-dimethylphosphino-indene, Compound 3

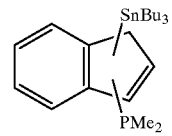

3

150 ml of ether were introduced into a round-bottomed flask which contained 5.5 g (0.047 mol) of indene; the mixture was cooled to −20° C. 20.8 ml of a 2.3 molar solution of butyl-lithium in hexane (0.048 mol) were added to this solution in the course of 5 minutes, a yellow solution being formed. After removal of the cooling bath, the solution was warmed to room temperature and subsequently stirred for 1 hour. After the reaction mixture had been cooled to −30° C., 4.6 g of chlorodimethylphosphine (0.048 mol) in 30 ml of ether were added in the course of 20 minutes, a precipitate forming. After stirring at −20° C. for 2 hours, 20.8 ml of a 2.3 molar solution of butyl-lithium in hexane (0.048 mol) were added drop-wise. When the addition was complete, the cooling bath was removed and the solution was warmed slowly to room temperature and subsequently stirred for 1.5 hours. After the suspension had been cooled to 0° C., 15.6 g of chlorotributyltin (0.048 mol) were added dropwise. The suspension formed was warmed to room temperature and stirred for 1.5 hours. The ether was removed in vacuo and the crude product was dissolved again in hexane, the solution was filtered and the filtrate was dried in vacuo, 17.4 g of the compound 3 (yield: 78%) remaining as a heavy yellow oil. $^1$H NMR (400 MHz, $CD_2Cl_2$) δ 7.67 (d, J=7.5 Hz, 1 H), 7.47 (d, J=7.4 Hz, 1 H), 7.18 (m, 2 H), 6.83 (m, 1 H), 4.28 (s with Sn satellites, 1 H), 1.43–0.78 (m, 33 H). $^{31}$P NMR (161.9 MHz, $CD_2Cl_2$): δ-61.6 ppm.

Example 4

Dimethylphosphino-indenyl-zirconium trichloride, Compound 4

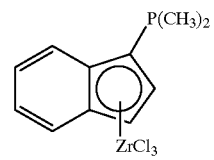

4

A solution of 17.0 g of the compound 3 (0.037 mol) in 50 ml of toluene was added to a suspension of 8.5 g (0.036 mol) of 99.9% pure $ZrCl_4$ in 200 ml of toluene at −78° C. When the addition was complete, the reaction mixture was stirred at −30° C. for 0.5 hour and then at 0° C. for 4 hours. The yellow precipitate formed was filtered off and washed with toluene and hexane. The solids were dried in vacuo, 8.3 g of the compound 4 (yield: 61%) remaining, as a free-flowing yellow powder. The powder was further purified by removal of the remaining tin compounds by means of extraction with toluene fed under reflux over a period of 3 hours under 30 mm Hg and then with pentane over a period of 2 hours in a Soxhlet extractor, 7.2 g (yield: 53%) of the product remaining. Because of the insolubility of this compound, no $^1$H NMR was obtained.

Example 5

Dimethylphosphino-dichloroboranyl-bridged indenyl-cyclopentadienyl-zirconium dichloride, Compound 5

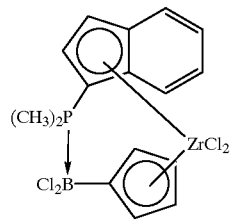

30 ml of toluene and 0.55 g of the compound 4 (0.0015 mol) were introduced into a Schlenk tube. 0.31 g (0.0014 mol) of the compound 2 were added to this suspension in the course of 5 minutes. The yellow suspension was stirred at room temperature for 6.5 hours, a slightly cloudy solution remaining. The precipitate was removed by filtration, a pale yellow toluene solution remaining. After removal of the toluene in vacuo, the product remained as a whitish solid. After the product had been washed with hexane and dried in vacuo, the compound 5 remained as a pale white solid (0.54 g; yield: 76%). $^1$H NMR (400 MHz, CD$_2$Cl$_2$) δ 7.84 (pseudo dd, J=7.4, Hz, 1.0 Hz, 1 H), 7.60 (m, 2 H), 7.51 (m, 1 H), 7.38 (m, 1 H), 6.93 (m, 1 H), 6.71 (m, 1 H), 6.66 (m, 1 H), 6.49 (m, 1 H), 6.30 (br s, 1 H), 2.11 (d J$_{H-P}$=11.9 Hz, 3 H), 1.94 (d, J$_{H-P}$=11.9 Hz, 3 H). $^{31}$P NMR (161.9 MHz, CD$_2$Cl$_2$)-5.9 (br, m); $^{11}$B (80 MHz, CD$_2$Cl$_2$) δ-14.6 (br d, J$_{B-P}$=126 Hz).

Example 6

Ethene-norbornene Copolymerization 54 ml of dry oxygen-free toluene and 47 g (0.5 mol) of norbornene distilled over sodium in a stream of argon were initially introduced into a V4A steel autoclave which had been heated thoroughly in vacuo, and 6.6 ml of a 10% strength MAO solution in toluene (10 mmol) were injected. The autoclave, which was stirred with a magnetic core, was heated to 70° C. under 6 bar of ethene and, after about 15 minutes, the copolymerization was started by addition of the catalyst under pressure by means of a pressure sluice. The catalyst employed was 1×10$^{-6}$ mol of [(ind)Me$_2$PBCl$_2$(Cp)ZrCl$_2$] (compound 5) in 0.52 ml of toluene and 1×10$^{-4}$ mol of MAO in 6.6 ml of 10% strength MAO/toluene solution, after preforming at room temperature for 15 minutes. After copolymerization at 70° C. under 6 bar of ethene for 5 hours, the mixture was cooled to RT, the autoclave was let down and the clear, viscous polymer solution was stirred slowly into 2 liters of acetone. The white polymer which had precipitated was filtered off, washed with acetone and extracted by stirring overnight in 2 liters of ethanol and 200 ml of concentrated aqueous hydrochloric acid, and the product was filtered off by means of a suction filter and rinsed with ethanol. It was then dried to constant weight at 120° C.

Polymer yield: 16.5 g

Catalyst activity: 16.5 tonnes of copolymer per mole of catalyst

Limiting viscosity in ortho-dichlorobenzene at 140° C. [η]=0.70 dl/g

Copolymer composition: 50 mol % of norborene, 50 mol % of ethene from the $^{13}$C-NMR in o-dichlorobenzene.

The DSC measurement (2nd heating up) demonstrates an amorphous copolymer without a melting peak and with a glass transition temperature Tg=152° C.

What is claimed is:

1. A process for the preparation of a cycloolefin (co)polymer for use for optical data memories by (co)polymerization of monomers from the group consisting of cyclic olefins, α-olefins having 2 or more C atoms and optionally conjugated or non-conjugated diolefins in the gas, bulk, solution, or slurry phase at −78 to +200° C. under 0.5 to 70 bar in the presence of organometallic catalysts which can be activated by a cocatalyst, which comprises employing as the organometallic catalyst a metallocene compound of the formula

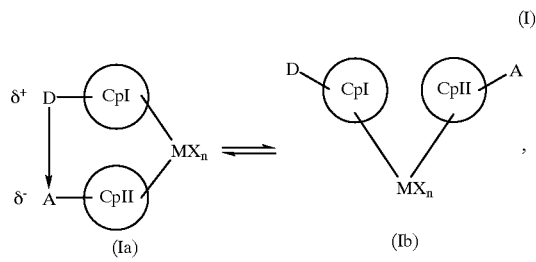

(I)

in which

CpI and CpII are two identical or different carbanions having a cyclopentadienyl-containing structure, in which one to all the H atoms can be replaced by identical or different radicals from the group consisting of linear or branched C$_1$–C$_{20}$-alkyl, which can be monosubstituted to completely substituted by halogen, mono- to trisubstituted by phenyl or mono- to trisubstituted by vinyl, C$_6$–C$_{12}$-aryl, halogenoaryl having 6 to 12 C atoms, organometallic substituents, including silyl, trimethylsilyl or ferrocenyl, or one or two can be replaced by D and A, D denotes a donor atom, which can additionally carry substituents and has at least one free electron pair in its bond state, A denotes an acceptor atom, which can additionally carry substituents and has an empty orbital capable of accepting a pair of electrons in its bond state, wherein D and A are linked by a reversible coordinate bond such that the donor group assumes a positive charge and the acceptor group assumes a negative charge, M represents a transition metal of sub-group III, IV, V or VI of the Periodic Table of the elements, including the lanthanides and actinides, X denotes one anion equivalent and n denotes the number zero, one, two, three or four, depending on the charge of M, or a π complex compound, or in metallocene compound of the formula

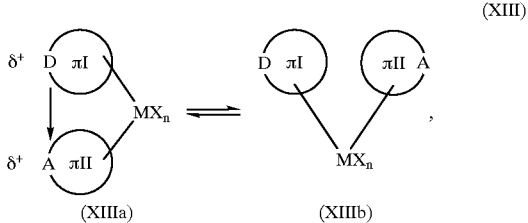

(XIII)

(XIIIa)   (XIIIb)

in which
- πI and πII represent different charged or electrically neutral π systems which can be fused with one or two unsaturated or saturated five- or six-membered rings,
- D denotes a donor atom, which is a substituent of πI or part of the π system of πI and has at least one free electron pair in its bond state,
- A denotes an acceptor atom, which is a substituent of πII or part of the π system of πII and has an empty orbital capable of accepting a pair of electrons in its bond state,
- wherein D and A are linked by a reversible coordinate bond such that the donor group assumes a positive charge and the acceptor group assumes a negative charge, and where at least one of D and A is part of the associated π system,
- wherein D and A in turn can carry substituents,
- wherein each π system and each fused-on ring system can contain one or more D or A or D and A and
- wherein πI and πII in the non-fused or in the fused form, one to all the H atoms of the π system independently of one another can be replaced by identical or different radicals from the group consisting of linear or branched $C_1$–$C_{20}$-alkyl, which can be monosubstituted to completely substituted by halogen, mono- to trisubstituted by phenyl or mono- to trisubstituted by vinyl, $C_6$–$C_{12}$-aryl, halogenoaryl having 6 to 12 C atoms, organometallic substituents including silyl, trimethylsilyl or ferrocenyl, or one or two can be replaced by D and A, so that the reversible coordinate D→A bond is formed (i) between D and A, which are both parts of the π system or the fused-on ring system, or (ii) of which D or A is part of the π system and in each case the other is a substituent of the non-fused π system or the fused-on ring system or (iii) both D and A are such substituents,
- wherein the case of (iii) at least one additional D or A or both is (are) parts of the π system or of the fused-on ring system,
- M and X have the above meanings and
- n denotes the number zero, one, two, three or four, depending on the charges of M and those of π-I and π-II.

2. The process as claimed in claim 1, wherein the metallocene compound or the π complex compound is employed as the catalyst in an amount of $10^1$ to $10^{12}$ mol of monomers per mole of metallocene or π complex compound.

3. The process as claimed in claim 1, wherein the reaction is carried out in the presence of a solvent selected from the group consisting of aromatic hydrocarbons, saturated hydrocarbon, aromatic halohydrocarbons and saturated halohydrocarbons.

4. The process as claimed in claim 1, wherein, in the metallocene compound the carbanions CpI and CpII or the π system πI denote a cyclopentadienyl skeleton slected from the group consisting of cyclopentadiene, substituted cyclopentadiene, indene, substituted indene, fluorene and substituted fluorene, in which 1 to 4 substituents slected from the group consisting of $C_1$–$C_{20}$-alkyl, $C_1$–$C_{20}$-alkoxy, halogen, $C_6$–$C_{12}$-aryl, halogenophenyl, D and A, wherein D and A are present per cyclopentadiene or fused-on benzene ring, it being possible for fused-on aromatic rings to be partly or completely hydrogenated.

5. The process as claimed in claim 1, wherein, in the metallocene compound, elements selected from the group consisting of N, P, As, Sb, Bi, O, S, Se, Te, F, Cl, Br and I are present as donor atoms D.

6. The process as claimed in claim 1, wherein, in the metallocene compound, elements selected from the group consisting B, Al, Ga, In and Tl are present as acceptor atoms A.

7. The process as claimed in claim 1, wherein in the metallocene compound or π complex compound, donor-acceptor bridges selected from the group consisting of

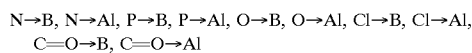

are present.

8. The process as claimed in claim 1, wherein, in the metallocene compound, M represents Sc, Y, La, Sm, Nd, Lu, Ti, Zr, Hf, Th, V, Nb, Ta or Cr.

9. The process as claimed in claim 1, wherein the metallocene compound or π complex compound is employed as a catalyst system together with cocatalysts selected from the group consisting of an aluminoxane, a borane, and a borate and, optionally, further cocatalysts and/or metal-alkyls.

10. The process as claimed in claim 1, wherein a rearrangement product of a metallocene compound or π complex compound is employed with self-activation, with which, after opening of the D/A bond, the acceptor atom A bonds an X ligand to form a zwitterionic metallocene complex structure or π complex structure, where a positive charge is generated in the transition metal M and a negative charge is generated in the acceptor atom A, and where a further X ligand represents H or substituted or unsubstituted C, in the bond of which to the transition metal M the olefin insertion takes place for the polymerization, 2x ligands being linked to a chelate ligand.

11. The process as claimed in claim 1, wherein said π complex compound is employed in which one of the atoms D or A is part of the ring of the associated π system, preferably D is part of the ring of the associated π system.

12. The process as claimed in claim 1, wherein an ionizing agent is reacted with said metallocene compound or π complex according to formula (I) or (XIII) to form a reaction product of the formula (XIa) to (XId)

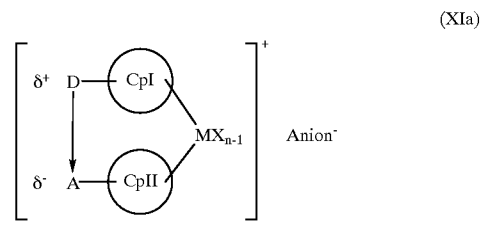

(XIa)

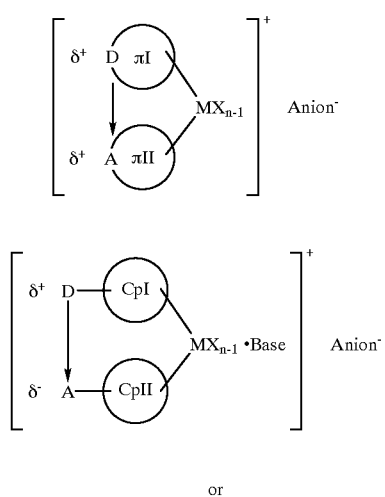

(XIb)

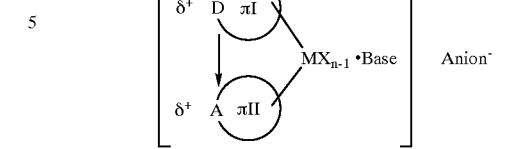

(XIc)

(XId)

in which
Anion represents the entire bulky, poorly coordinating anion and Base presents a Lewis base is employed.

13. The process according to claim 5, wherein, in the metallocene compound, elements selected from the group consisting of N, P, O and S are present as donor atoms D.

14. The process according to claim 6, wherein, in the metallocene compound, elements selected from the group consisting of B, Al, and Ga, are present as acceptor atoms A.

15. The process according to claim 8, wherein, in the metallocene compound, M represents Ti, Zr, Hf, V, Nb or Ta.

* * * * *